(12) United States Patent
Gaylard et al.

(10) Patent No.: US 9,007,936 B2
(45) Date of Patent: Apr. 14, 2015

(54) SYSTEM AND METHOD FOR STABILIZING A WIRELESS MONITORING NETWORK

(75) Inventors: Nigel Gaylard, Perth (AU); John Hines, Cheshire (GB); Dean Limbert, Derby (GB)

(73) Assignee: DebMed USA LLC, Charlotte, NC (US)

( * ) Notice: Subject to any disclaimer, the term of this patent is extended or adjusted under 35 U.S.C. 154(b) by 333 days.

(21) Appl. No.: 13/427,467

(22) Filed: Mar. 22, 2012

(65) Prior Publication Data

US 2013/0250823 A1 Sep. 26, 2013

(51) Int. Cl.
*H04W 40/14* (2009.01)
*H04W 4/00* (2009.01)
*H04W 40/24* (2009.01)
*G06F 19/00* (2011.01)
*G08B 21/24* (2006.01)
*H04W 84/18* (2009.01)
*H04L 29/08* (2006.01)

(52) U.S. Cl.
CPC .......... *H04W 4/005* (2013.01); *H04W 40/242* (2013.01); *H04W 40/244* (2013.01); *G06F 19/327* (2013.01); *G08B 21/245* (2013.01); *H04W 84/18* (2013.01); *H04L 67/12* (2013.01)

(58) Field of Classification Search
CPC .... H04L 45/02; H04W 4/005; H04W 40/242; H04W 40/244; H04W 40/248; H04W 84/18
USPC ......................................... 370/238, 252–255
See application file for complete search history.

(56) References Cited

U.S. PATENT DOCUMENTS

| 7,808,960 | B1 * | 10/2010 | Chan et al. .................... 370/338 |
| 2010/0008272 | A1 | 1/2010 | Messinger et al. |
| 2011/0149858 | A1 * | 6/2011 | Hwang et al. ................. 370/328 |

FOREIGN PATENT DOCUMENTS

WO      0249272 A2      6/2002

OTHER PUBLICATIONS

Patrick Kinney, "ZigBee Technology: Wireless Control that Simply Works", Communications Design Conference, Oct. 2, 2003, Kinney Consulting LLC.
C. Hedrick, Rutgers University, "Routing Information Protocol", Jun. 1988.
International Search Report for corresponding Application No. PCT/IB2013/000762, dated Jul. 30, 2013 (10 pages).
Notification Concerning Transmittal of International Preliminary Report on Patentability (Chapter 1 of the Patent Cooperation Treaty), and International Searching Authority for corresponding Application No. PCT/IB2013/000762, dated Oct. 2, 2014 (8 pages).

* cited by examiner

*Primary Examiner* — Pao Sinkantarakorn
(74) *Attorney, Agent, or Firm* — McAndrews, Held & Malloy, Ltd.

(57) ABSTRACT

Stabilization of a wireless information collection system for dispenser usage compliance in a facility is provided. This system and method enable network stabilization by providing a network "heartbeat." The network stabilization operates independently from information collection. Therefore, the system and method are able to improve the reliability of wireless information collection systems where the frequency of data collection is not steady.

18 Claims, 6 Drawing Sheets

SYSTEM AND METHOD FOR STABILIZING A WIRELESS MONITORING NETWORK

FIELD OF THE INVENTION

This invention relates to a system and method for wirelessly monitoring dispenser usage in a facility and in particular to stabilizing a wireless network for monitoring the dispenser usage.

BACKGROUND OF THE INVENTION

The spread of healthcare acquired infections also known as HAI's has been an ever increasing challenge in health care facilities. HAI's include the transmission of bacteria, viruses and other disease-causing micro-organisms from various sources such as a patient or environmental surfaces to another patient or surface via the hands of healthcare workers which results in an infection of a patient that was previously not infected. These problems have been more apparent in recent years with the SARS (severe acute respiratory syndrome) outbreak and the influenza A virus H1N1 pandemic. As well, health care facilities have battled MRSA (methicillin-resistant staphylococcus aureus) and VRSA (vancomycin-resistant staphylococcus aureus) and other drug resistant micro-organisms for many years. Accordingly, there is a need to ensure that health care professionals comply with hand hygiene best practices. Hand hygiene can be accomplished using liquids such as a sanitizing product which does not require water for rinsing off or alternatively it can be accomplished using a soap and water.

As well there are other types of liquids that can be dispensed such as sun screen. The use of the sun screen may need a similar system and method of monitoring, tracking and reporting. For example such a method could be very important in schools in Australia where the incidences of skin cancer are very high.

A need exists for a system and method to reliably monitor, track and report dispenser usage. Such a system should be low-cost, stable and reliable. ZigBee is a low-power, wireless network standard that may offer reliability. However, ZigBee requires network coordinators along with routers to establish the network. This additional level of hardware adds both complexity and cost to a system. Therefore, there is the need for a reliable routing protocol for a wireless network that is tailored to improving the stability for low data flow without the use of network coordinators.

SUMMARY OF THE INVENTION

A wireless information collection system for dispenser usage compliance within a group of interest in a facility is provided. The information collected may include the type of product in the dispenser. The type of product could be one of hand soap, sanitizer, lotion, cream, sunscreen and body wash.

The group of interest may be one of a medical unit, a surgical unit, a critical care unit, an intensive care unit, an emergency care unit, a pediatric unit, an emergency unit, an outpatient unit, a specialty care unit, a dermatology unit, an endocrinology unit, a gastroenterology unit, an internal medicine unit, an oncology unit, a neurology unit, an orthopedic unit, an ophthalmic unit, an ear nose and throat unit, a neonatal unit, an obstetrics and gynecology unit, a cardiac unit, a psychiatric unit, a post-operative recovery unit, a radiology unit, a plastic surgery unit and an urology unit. The group may also be one of a bed, a room, a ward, a unit, a floor, a facility and a hospital group.

The facility may be one of a health care facility, a food processing facility, a food service facility, an educational facility and a manufacturing facility. Alternatively, the facility type may be one of a teaching hospital, a non-teaching hospital, a long term care facility, rehabilitation facility, a free standing surgical center, a health care professional office, a dental office, a veterinarian facility and a community care facility.

The wireless information collection system may comprise dispensers, hubs, and at least one gateway. Each hub may receive data from up to 10,000 dispensers and the distance between each dispenser and its associated hub may be up to one mile. The wireless information collection system may communicate in one or more of the industrial, scientific and medical (ISM) radio bands. ISM radio bands include, for example, 400-450 MHz, 850-950 MHz, and 2.4-2.5 GHz. Transmission power may be 1 watt or less.

The wireless information collection system may comprise an ad-hoc wireless network to allow for the installation and removal of dispensers. To ensure that infrequent data messages are passed reliably, a system and method is required maintain active connections independent of data flow.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
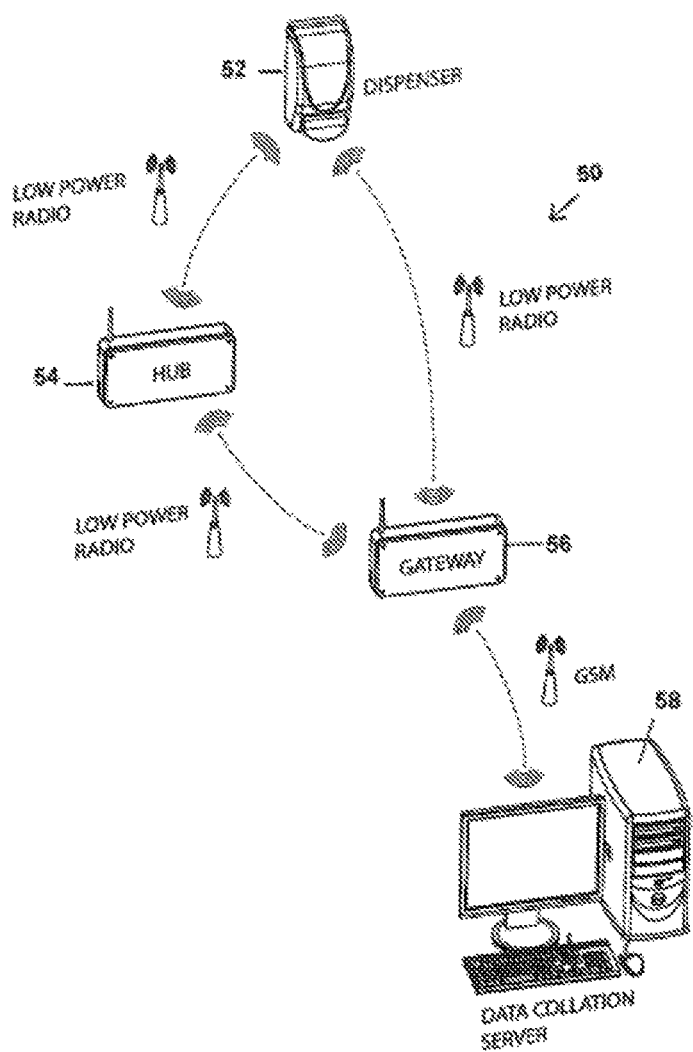
FIG. 1 is a diagram showing a wireless information collection system in accordance with the present invention.

Measuring healthcare worker adherence to hand hygiene compliance guidelines is not a simple matter. There are no proven standards or benchmarks that may be used. However there is a very clear need to monitor and measure hand hygiene compliance. Accordingly there is a need to determine whether or not a hand hygiene action occurred when there was an indication for a hand hygiene action. Hand hygiene actions can be sanitizing with a sanitizing product which does not require water for rinsing off or alternatively it can be washing with soap and water.

There are a number of ways to measure compliance—namely direct observation, remote observation, self-reporting and dispenser usage data or product usage data. Each way has its own benefits and challenges. Specifically direct observation provides specific information on hand hygiene behaviors, techniques and indication. However, the labor and resources required to collect such data is intensive. Generally if this type of data is collected it is only collected for a small sample of the total of hand hygiene opportunities and thus has a typically low level of statistical reliability. The data is also subject to bias from over or under sampling of certain shifts and units. As well, it has been shown that there are also issues regarding observer reliability and therefore it is difficult to compare the results from one observer with another.

In regard to remote observation, such as video, the advantage is that it is less subject to bias and it can operate at any time of day or night and in any unit. However, such a method of data collection is expensive because of the installation and maintenance of the video equipment as well as the time to review the video, such review is then subject to the same lack of observer reliability as direct observation. Further, it can be subject to bias based on the video location. Further, there may be privacy issues in regard to video locations.

In regard to the self-reporting option, this has the advantage of being low cost and it encourages health care workers with respect to hand hygiene self-awareness. However, in general this type of data collection has poor reliability and most experts in the field consider this method of little, if any, value.

In typical healthcare environments, hand hygiene liquids are stored and dispensed onto the hands from dispensers. Therefore, there is a direct correlation between dispenser usage or activations and hand hygiene events being performed. Dispenser usage data can provide the product volume used per patient day or the number of times the dispenser was used per patient day. This has the advantage of being less costly to monitor and it is not subject to selection bias. Dispenser usage information can be collected manually or electronically. Electronically monitoring dispenser usage: 1) allows organization-wide trends to be tracked over time; 2) can be unobtrusive and designed to take up little additional space; 3) can be used across all shifts, twenty-four hours a day, and seven days a week; 4) requires minimal staff training; and 5) can be done in many different healthcare settings.

In the embodiments herein the dispensers are capable of determining when they are activated. A plurality of activations within a short period of time may indicate that one user has activated the dispensers a plurality of times rather than multiple users activating the dispenser very close together. Therefore, a plurality of activations within a predetermined activation period may be considered a single dispenser usage event. For example, a plurality of activations within a 1 to 4 second time frame will be considered a single dispenser usage event. For hand soaps and hand sanitizers in a healthcare facility, this may be set at 2.5 seconds. However, where dispenser usage is being monitored for different types of products in different types of facilities, this may be set for a different activation period. Typically dispensers are calibrated to dispense a predetermined amount of liquid per activation. Accordingly, the dispenser activation directly relates to product usage.

FIG. 1 is a diagram showing a wireless information collection system in accordance with the present invention. System 50 is a dispenser usage monitoring system that comprises at least one dispenser 52, a wireless monitoring network, and a data collation server 58. The dispenser 52 comprises a transmitter that wirelessly reports dispenser use to the wireless monitoring network that, in turn, forwards dispenser transmissions to the data collation server 58. The wireless monitoring network is created by at least one hub 54 and at least one gateway 56.

In the wireless system 50 the dispenser 52 is wirelessly connected to a hub 54 and/or a gateway 56. The gateway is connected to a data collation server 58. Data may be sent from the gateway 56 to the server 58 in a burst by way of a wired network (e.g., the internet) and/or any cellular network such as GSM. Collected data may also be sent to an offsite server for data processing.

Each dispenser 52 has a sensor therein and may be capable of storing data related to up to 100 or more activations. It will be appreciated by those skilled in the art that 100 activations is by way of example only and that typically each dispenser may need to only store data relating to a few activations. This minimizes the chance of losing data in the event of queuing for receipt by the hub 54. The data is sent between the dispenser 52 and the hub 54 and between the hub 54 and the gateway 56 in bursts which may be time or memory dependent.

When a dispenser usage event occurs, the dispenser may wait 2.5 seconds, for example, to monitor for repeated dispenser actuations.

Before a dispenser is able to transmit a message it first attaches itself to a hub or gateway device. This is done through a broadcast event that is replied to by any hubs or gateways within range. The reply includes the address of the hub or gateway and the current time in UTC format. This is sometimes referred to as a "handshake." If an acknowledgement is not received by the dispenser, the dispenser will retry until it receives an acknowledgement from a hub. The dispenser may transmit connection inquiries and repeat up to 10 times at 2 second intervals is no hub responds.

The dispenser saves the address of the hub or gateway with the highest received signal strength and resets its clock to the received timestamp.

If a broadcast is not successful then the existing time is left as is, but the address for communications is reset to indicate to the dispenser that no valid radio path exists.

The hubs send the dispenser usage data on through the hub network until the data reaches a gateway. Each successive hub in the chain acknowledges receipt of the dispenser usage data from the previous hub. If an acknowledgement is not received by the originating hub, it will retry until successful. The hubs within the transmission distance of the gateway transmit the dispenser usage data to the gateway. When the dispenser usage data is captured by the gateway, it transmits an acknowledgement back to the originating hub.

The gateway 56 collates all of the data it received from the rest of the system into transmission "packets" of a predetermined size. These data "packets" are transmitted to the data collation server 58. The data may be sent to the collation server 58 wirelessly and/or over the internet. When the data "packet" is received or captured by the data collation server 58 an acknowledgement is sent back to the gateway 56. If an acknowledgement is not received by the gateway 56, it will retry until successful. This type of system does not require an access point and is often referred to as an ad-hoc network or a mesh network.

The dispenser connects to a hub in the order of the hub's response to a connection inquiry by the dispenser. Hubs respond to dispensers after receiving the connection inquiry. The hub responses may be delayed based on the signal strength of the connection inquiry—a longer delay for a weaker signal. The weaker signal may be less reliable as it may indicate a farther distance traveled or a more obstructed transmit path. For example the response delay may be computed as:

Response Delay=950 milliseconds−(Signal Strength*10)  EQ. 1 where the Signal Strength is measured in dB. If signal strength is greater than 20 dB, a shorter delay may be computed, for example:

Response Delay=50 milliseconds+(100−signal strength)  EQ. 2

A gateway will acknowledge a hub in the same manner as a hub acknowledges another hub. The dispenser transmitter shuts off when a transmission is acknowledged by the hub. Each transmission comprises an actuation identification number that is sequentially assigned. Therefore, a lost actuation can be identified as missing.

Dispensers are positioned around the facility being monitored. Hubs are positioned around the facility within range of the dispensers such that each dispenser is in range of at least one hub. As described above, when each dispenser 52 is used, it will transmit its unique identification code, date and time to the hub or hubs 54, the hubs 54 in turn transmit the data to a gateway 56 and then to a server 58. The server 58 may be on site or off site. In a large facility, the system may use a mesh network. At each stage of data transmission there will be a "handshake" between the transmitter and receiver whether that be dispenser and hub; hub and hub; hub and gateway; or gateway and server. A handshake confirms the data is received and instructs the transmitting device (e.g., dispenser, hub or gateway) to delete the information from the memory.

Accordingly, when designing the system herein for healthcare facility usage, for example a hospital, there are a number of competing interests. Specifically the system will require a plurality (e.g., 1,000's) of battery powered activation sensors which need to reliably transmit usage data wirelessly around a sprawling hospital building. The system must not interfere with medical equipment, comply with regulatory requirements and preferably utilize license free radio frequencies.

Hubs may be hard-wired to electrical power since they constantly listen for dispenser activations and maintain the network communication. Dispenser transmitters can be battery powered to allow more economical installation.

The group monitoring system for dispenser usage data collection may include a plurality of dispensers and a plurality of hubs. Each hub may be capable of receiving data from up to 10,000 dispensers. The distance between each dispenser and its associated hub is typically no greater than one mile, and the data is transmitted over a frequency between 850 and 950 MHz.

When changes are made to the network and/or messages are not transmitted frequently, the preferred pathways may be changed and/or become unreliable. Therefore, hubs must maintain reliability of connections (i.e. stability) independent of the data flow. To accomplish this stability, hubs broadcast a "heartbeat." For example, every 5 minutes each active hub may broadcast a beacon to find routes to the gateway to maintain communication connections An active hub is required, on power up, to establish a route to a gateway prior to accepting any messages either from other hubs or dispensers. In order to do this the active hub broadcasts a beacon and then stores the addresses from the receiving hubs or gateways in a list including the number of hops that the active hub has to a gateway. The active hub then selects the most direct route to the gateway based on the number of hops.

Figure 2:
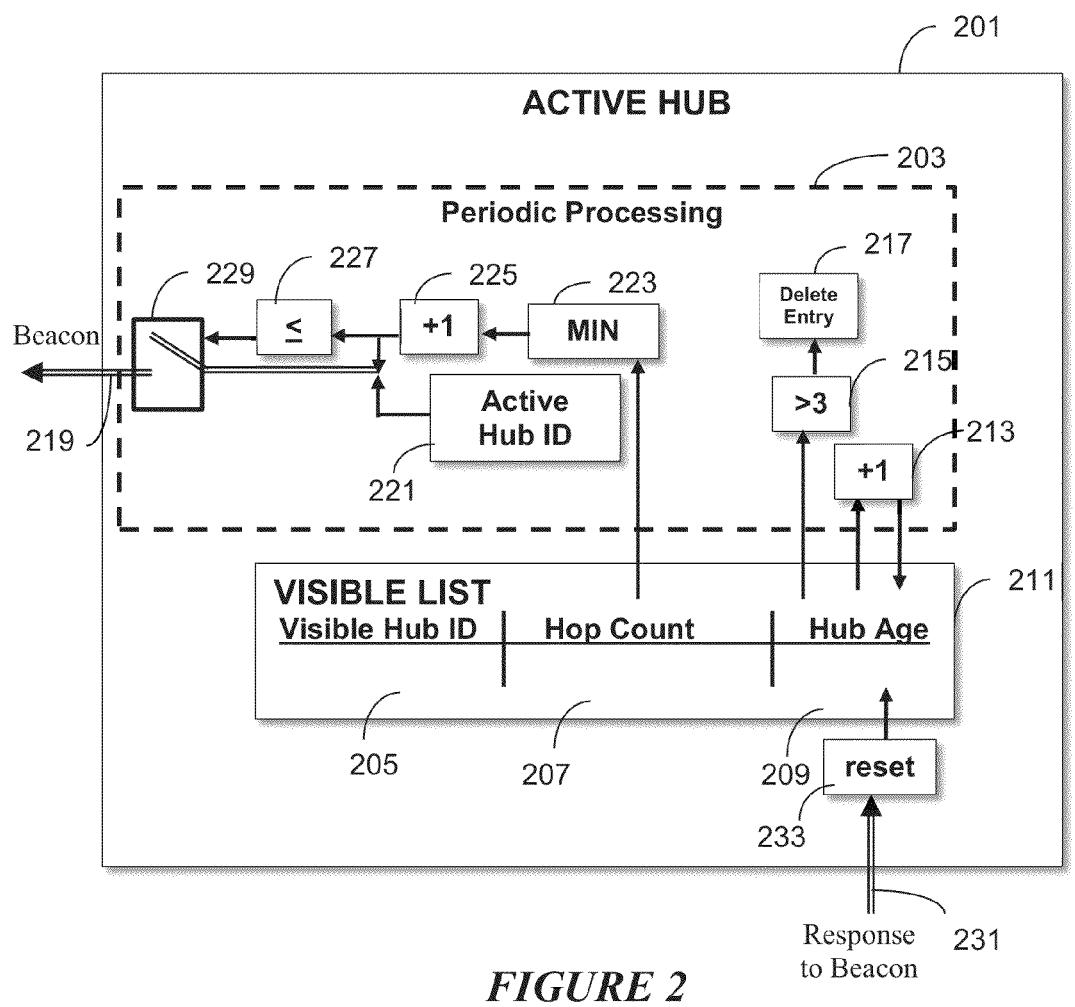
FIG. 2 is a diagram showing an active hub in accordance with the present invention.

FIG. 2 is a diagram showing an active hub 201 in accordance with the present invention. The active hub 201 comprises a visible list 203. The visible list is a list of all other hubs that are "visible" and their number of hops 207 to a gateway, where the nearest gateway is the only destination on the network. Each entry in the visible list 203 corresponds to a route and comprises a visible hub ID 205, a hop count 207, and a hub age 209.

The visible list may have a fixed number of route entries to reduce system complexity. For example, the visible list may be fixed at 10 entries long. Route entries visible list may be associated with the smallest hop counts and/or the visible hubs that respond with the least delay. The route with the least hops is preferred and should be selected first.

When a hub or gateway broadcast has not been seen for 3 times the broadcast interval (i.e. 15 minutes) it may be deleted from the visible list. The maximum number of hops allowed may be set to 5 in order to minimize the convergence time when a problem (such as a loop) occurs.

Every message forwarded has a "hop count" indicator that is incremented. If the number of hops indicated is above a route threshold, the hub sets this route via its visible list to infinite (but retains the message). This forces hubs to break a possible loop. When the same transmitted message is received back from a listed hub, the number of hops associated with the listed hub in the visible list is marked as infinite.

Hubs will retry to send messages through their preferred route 10 times before switching to the next most suitable route from the visible, to increase system stability. A running measure of transmission failure may be kept. For example, a transmission failure will increase (i.e. by 3) the running measure, and a transmission success will decrease (i.e. by 1) the running measure. When the running measure of transmission failure reaches a maximum value (i.e. 30) the route is dropped.

On a periodic basis, all hubs with at least one valid route will broadcast their status, which includes a candidate route indicating a number of hops. Inactive hubs do not have a valid route, so no periodic broadcasts are carried out and no hub messages are acknowledged unless a hub is active or live. The active hub 201 will operate to periodically process 203 data in its visible list 211. For example, every 5 minutes the active hub 201 will broadcast a beacon 219 comprising an active hub ID 221 and a candidate route. A longer broadcast interval may be used to minimize radio traffic.

The candidate route is the minimum number of hops from the receiving hub to the gateway if a first hop is to the active hub 201. Since the minimum hop count from the active hub to the gateway is stored in the visible list of the active hub, the candidate route is equal to the minimum 223 hop count 207 in the visible list 203 of the active hub 201 plus one 225 to account for the hop from the receiving hub to the active hub 201. A hub may only broadcast 229 if the candidate route is less than a route threshold 227. For example, routes may be limited to 5 hops or less.

The hub age 209 of each route entry in the visible list 203 of the active hub 201 will be periodically incremented 213. When a route entry has an age that exceeds the age threshold 215, that route will be deleted 217. For example, the age threshold may be 3 beacon intervals or 15 minutes. If a route has not been received in 15 minutes, the route may be unavailable.

The active hub 201 may receive a response to the beacon 231, and the hub age of the route entry associated with the response 231 may be reset. This broadcast timer is reset, since the route has proven to be valid.

Figure 3:
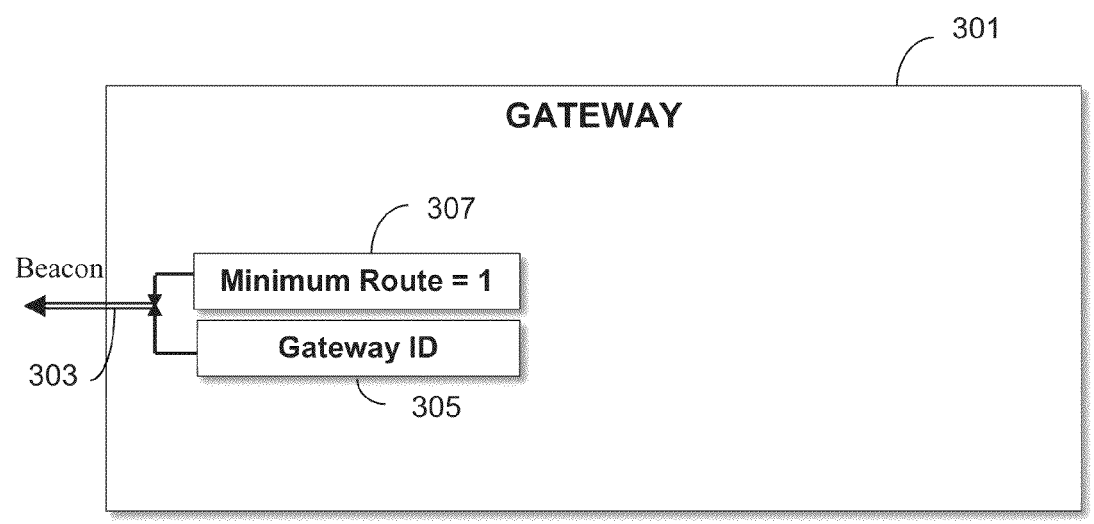
FIG. 3 is a diagram showing a gateway in accordance with the present invention.

FIG. 3 is a diagram showing a gateway in accordance with the present invention. A gateway 301 may broadcast a beacon 303 in the same way as the active hub 201. The gateway beacon may comprise a gateway ID 305 and a candidate route 307. However, the candidate route 307 of the gateway 301 will always be set the same value. The direct route from a receiving hub+ to the gateway is one hop.

Figure 4:
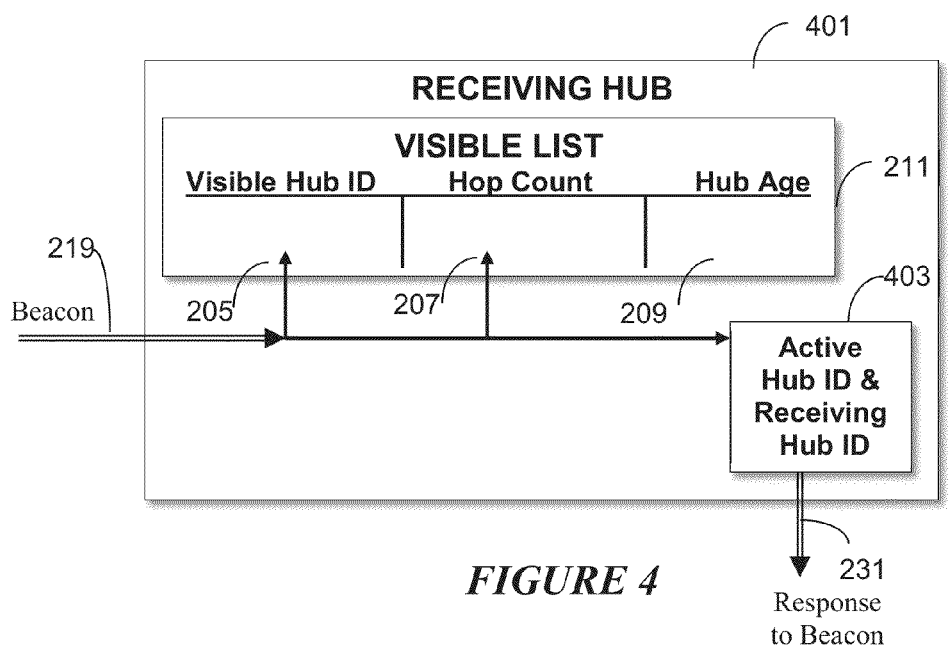
FIG. 4 is a diagram showing a receiving hub in accordance with the present invention.

FIG. 4 is a diagram showing a receiving hub in accordance with the present invention. A receiving hub 401 is a hub that receives a beacon 219 from the active hub 201. A hub may operate as an active hub and a receiving hub, in that the active hub may receive a beacon from another active hub.

Upon receipt of the beacon 219 from the active hub 201, the receiving hub 401 may transmit a response 231. This response 231 may comprise the active hub ID and the receiving hub ID 403. The response may be delayed according to the beacon's signal strength measurement as described above with reference to EQ. 1 and EQ. 2.

The active hub will transmit route update information after the broadcast. For example, route update information may be transmitted 3 seconds after the broadcast from the active hub. The receiving hub 401 may update its visible list 211 according to the route update information. The receiving hub 401 may add a route entry associated with the active hub ID 205 and the hop count 207 of the broadcasted candidate route may be saved. The hub age 209 of the route entry associated with the active hub may be initialized. If the visible list 211 of the receiving hub 401 already has a route entry associated with the active hub 201, the receiving hub 401 may need to update the hop count 207 associated with the active hub if the hop count associated with the active hub has changed.

Figure 5:
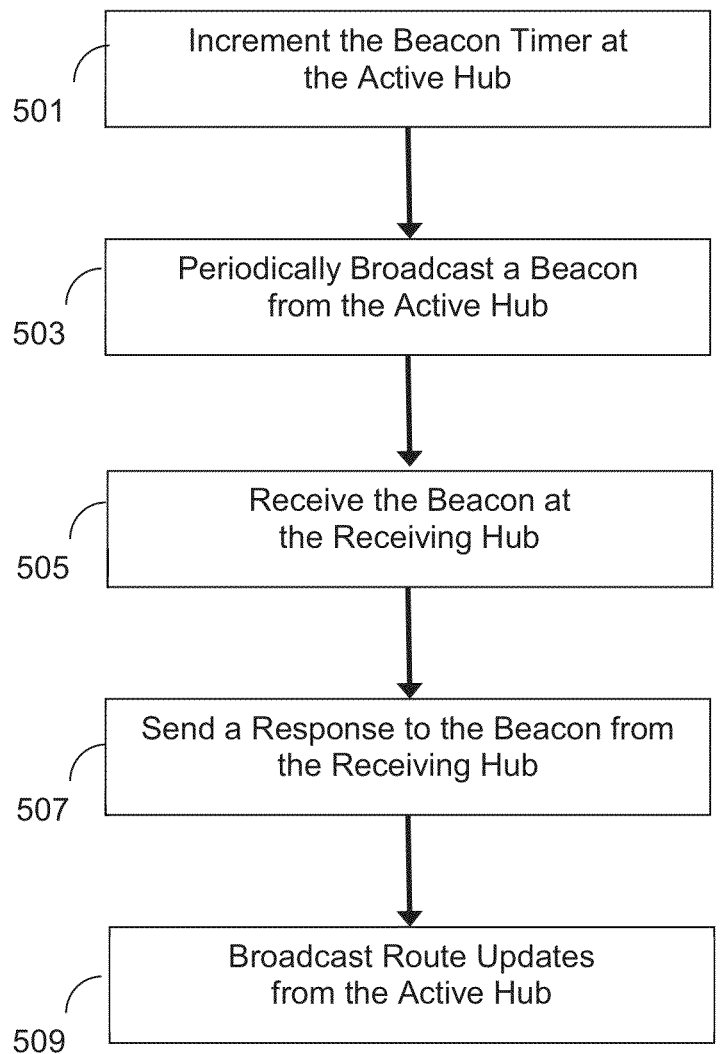
FIG. 5 is flow chart showing a method for stabilizing a wireless network in accordance with the present invention.

FIG. 5 is flow chart showing a method for stabilizing a wireless network that operates to monitor dispenser usage in a facility. Network stabilization enables a higher level of overall system performance and minimizes the number of missed messages from the dispensers.

A hub age of each route entry in a visible list of an active hub is periodically incremented according to the beacon timer at 501. The active hub is a hub that has at least one route entry stored in the visible list. The route entry must be valid, in that the hop count must be less than a route threshold and the hub age must be less than an age threshold. For example, the route threshold may be set to a maximum of 5 hops, and the age threshold may be set to 3 broadcast intervals. Periodically the hub age, of each route entry, may be compared to the age threshold. The route entries, from the visible list, associated with a hub age that is above the age threshold may be removed.

A beacon is periodically broadcasted from the active hub at 503. The broadcast interval may be, for example, 5 minutes. The beacon comprises an active hub ID and a candidate route. The candidate route is the minimum number of hops from a receiving hub to a destination if a first hop is to the active hub, and the candidate route is equal to one plus the minimum hop count in the visible list of the active hub.

The destination for all routes is a gateway. The gateway will also broadcast a beacon with a candidate route corresponding to 1 hop.

At 505, a beacon is received at a receiving hub. The receiving hub responds to the beacon at 507. When the response is received by the active hub, the active hub may reset the hub age of the route entry associated with the receiving hub.

The active hub will broadcast route updates at 509. A visible list of the receiving hub may be updated according to the route updates. If the visible list of the receiving hub does not comprise a route entry associated with the active hub a route entry associated with the active hub may be added. If the visible list of the receiving hub does comprise a route entry associated with the active hub and the hop count associated with the active hub is not equal to the candidate route, the receiving hub may update the hop count associated with the active hub.

The visible list of the receiving hub and the visible list of the active hub may each comprise a fixed number of route entries. To reduce memory usage and system complexity, only the route entries associated with the smallest hop counts may be saved.

New dispensers, hubs and/or gateways may be added to the dispenser usage monitoring system. As well dispensers, hubs and/or gateways may be removed from the system. Dynamic system changes are accommodated through the protocol described herein. New hubs may be initialized with no valid routes. The visible list of a new hub is populated automatically by processing beacons and response. At startup only gateways are 'live' or 'active' to ensure stable startup scenarios.

Figure 6:
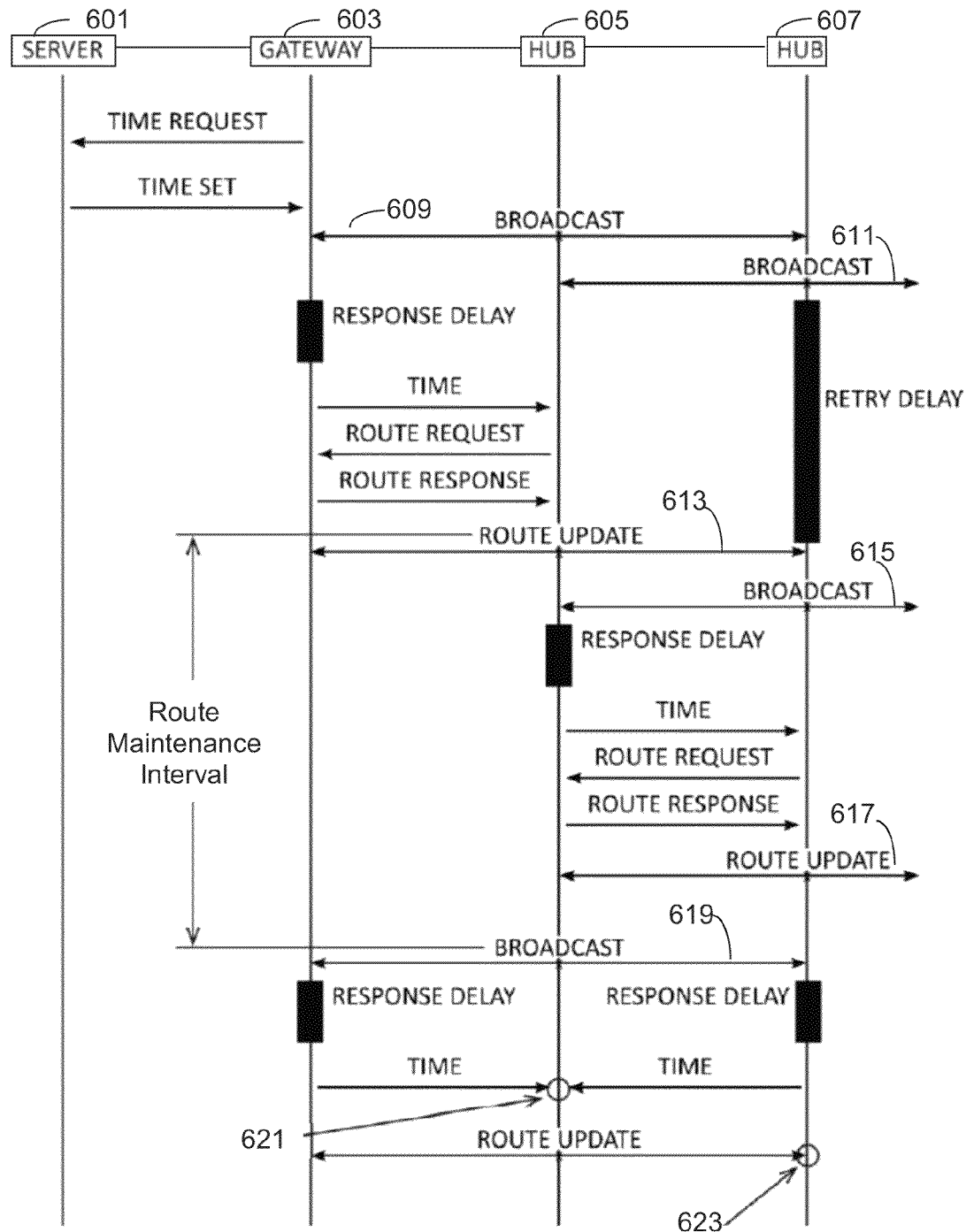
FIG. 6 is sequence diagram showing a method for stabilizing a wireless network in accordance with the present invention.

FIG. 6 is sequence diagram showing a method for stabilizing a wireless network in accordance with the present invention. This Unified Modeling Language (UML) sequence diagram 600 illustrates a network start-up scenario. For illustration of the disclosed embodiment, the network consists of a sever 601, a gateway 603, and two hubs—hub 605 and hub 607.

The UML sequence 600 shows both the establishing and the maintenance of the routes. When the network is initialized, gateway 603 is the only active wireless member. When hub 605 is introduced into the network, hub 605 will broadcast a beacon for the first time. The broadcast 609 from hub 605 is received by gateway 603 and hub 607. Gateway 603 will respond to the broadcast 609. However, hub 607 will not respond to the broadcast 609 since it is not yet active. Responses to broadcasts may be delayed. A response delay may be, for example, less than 4 seconds. The protocol for the broadcast response may comprise a TIME transfer, a ROUTE REQUEST, and a ROUTE RESPONSE.

When hub 607 is introduced into the network, hub 607 will broadcast a beacon for the first time. The broadcast 611 from hub 607 is received by hub 605. However, hub 605 will not respond to broadcast 611 until hub 605 has established a route to gateway 603. When hub 607 does not receive a response from hub 605, hub 607 will rebroadcast its beacon at 615. There may be a RETRY DELAY before a hub rebroadcasts. The RETRY DELAY may be, for example, 30 seconds.

The rebroadcast 615 by hub 607 is received by hub 605. Since the rebroadcast 615 follows a route update 613 by hub 605, hub 605 will respond to the rebroadcast 615 from hub 607. A route update 617 by hub 607 will follow this affirmative response from hub 605.

A second broadcast beacon 619 is sent by hub 605 after the route maintenance interval. Broadcasts from hubs continue periodically at a rate determined by the route maintenance interval. The route maintenance interval may be the same for all hubs and may be set to 5 minutes.

At point 621, hub 605 receives broadcast responses from gateway 603 and hub 607. These broadcast responses may be used to update the routing table at hub 605 and reset the associated route timers.

When hub 607 is notified, at 623, that the routing table of hub 605 has been updated, the entry associated with hub 605 in the routing table of hub 607 will be updated. However, this notification 623 may not reset the route timer in hub 607 associated with hub 605.

Embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a dispenser usage compliance system.

As used herein, the terms "comprises" and "comprising" are to be construed as being inclusive and open rather than exclusive. Specifically, when used in this specification including the claims, the terms "comprises" and "comprising" and variations thereof mean that the specified features, steps or components are included. The terms are not to be interpreted to exclude the presence of other features, steps or components.

What is claimed as the invention is:

1. A wireless system that operates to monitor wireless transmissions from one or more dispensers, the system comprising:
    a dispenser that operates to wirelessly communicate a usage event to at least one of a plurality of hubs;
    a receiving hub, in the plurality of hubs, that operates to:
        receive a beacon;
        transmit a response to the beacon; and
        update a visible list of the receiving hub according to the received beacon; and
    an active hub, in the plurality of hubs, that operates to periodically:
        increment a hub age of each route entry in a visible list of the active hub; and
        broadcast the beacon comprising an active hub ID and a candidate route,
    wherein the candidate route is the minimum number of hops from the receiving hub to a destination if a first hop is to the active hub, and the candidate route is equal to one plus the minimum hop count in the visible list of the active hub, and
    wherein the receiving hub is operable to update a hop count associated with the active hub if the hop count associated with the active hub is not equal to the candidate route.

2. The system of claim 1, wherein the receiving hub operates to add a route entry associated with the active hub and initialize a hub age of the added route entry, if the visible list of the receiving hub does not comprise a route entry associated with the active hub.

3. The system of claim 1, wherein the active hub comprises at least one route entry stored in the visible list, the at least one route entry comprises a hop count less than a route threshold, and the hub age of the at least one route entry is less than an age threshold.

4. The system of claim 1, wherein the active hub is operable to receive the response to the beacon.

5. The system of claim 4, wherein the active hub is operable to reset the hub age of the route entry associated with the response to the beacon.

6. The system of claim 1, wherein the destination is a gateway.

7. The system of claim 6, wherein the gateway is operable to broadcast a beacon with a candidate route corresponding to 1 hop.

8. The system of claim 1, wherein the visible list of the receiving hub and the visible list of the active hub each comprise a fixed number of route entries associated with the smallest hop counts.

9. The system of claim 1, wherein the receiving hub will not acknowledge the active hub if the active hub is not in the visible list.

10. The system of claim 1, wherein the active hub is operable to periodically compare the hub age, of each route entry, to an age threshold and remove the route entries, from the visible list, associated with a hub age that is above the age threshold.

11. A method for stabilizing a wireless network that operates to monitor dispenser usage in a facility, the method comprising:
    periodically incrementing a hub age of each route entry in a visible list of an active hub in a plurality of hubs;
    periodically broadcasting a beacon comprising an active hub ID and a candidate route, wherein the candidate route is the minimum number of hops from a receiving hub to a destination if a first hop is to the active hub, and the candidate route is equal to one plus the minimum hop count in the visible list of the active hub;
    receiving a beacon at a receiving hub, in the plurality of hubs;
    updating a visible list of the receiving hub according to the beacon;
    transmitting a response to the beacon;
    enabling communication to a dispenser that operates to wireless communicate a usage event to at least one of a plurality of hubs; and
    updating the hop count associated with the active hub if the hop count associated with the active hub is not equal to the candidate route.

12. The method of claim 11, wherein the method comprises adding a route entry associated with the active hub and initializing a hub age of the added route entry, if the visible list of the receiving hub does not comprise a route entry associated with the active hub.

13. The method of claim 11, wherein the active hub comprises at least one route entry stored in the visible list, the at least one route entry comprises a hop count less than a route threshold, and the hub age of the at least one route entry is less than an age threshold.

14. The method of claim 11, wherein method comprises resetting the hub age of the route entry associated with the response to the beacon.

15. The method of claim 11, wherein the destination is a gateway.

16. The method of claim 15, wherein method comprises broadcasting a beacon with a candidate route corresponding to 1 hop from the gateway.

17. The method of claim 11, wherein the visible list of the receiving hub and the visible list of the active hub each comprise a fixed number of route entries associated with the smallest hop counts.

18. The method of claim 11, wherein the method comprises periodically comparing the hub age, of each route entry, to an age threshold and removing the route entries, from the visible list, associated with a hub age that is above the age threshold.

* * * * *